US008052598B2

(12) United States Patent
Groszmann

(10) Patent No.: US 8,052,598 B2
(45) Date of Patent: Nov. 8, 2011

(54) SYSTEMS AND METHODS FOR CALIBRATING AN ENDOSCOPE

(75) Inventor: Daniel E. Groszmann, Cambridge, MA (US)

(73) Assignee: General Electric Company, Schenectady, NY (US)

( * ) Notice: Subject to any disclaimer, the term of this patent is extended or adjusted under 35 U.S.C. 154(b) by 913 days.

(21) Appl. No.: 11/546,799

(22) Filed: Oct. 12, 2006

(65) Prior Publication Data

US 2008/0091069 A1    Apr. 17, 2008

(51) Int. Cl.
*A61B 1/04* (2006.01)

(52) U.S. Cl. .................. 600/168; 600/167; 600/118

(58) Field of Classification Search .......... 600/109, 600/111, 117, 118, 166–168, 414, 417, 425–426, 600/429, 473, 475–477; 348/65, 468, 476, 348/698; 382/255
See application file for complete search history.

(56) References Cited

U.S. PATENT DOCUMENTS

| | | | | |
|---|---|---|---|---|
| 6,063,023 | A  * | 5/2000 | Sakiyama et al. | 600/118 |
| 6,511,418 | B2  | 1/2003 | Shahidi et al. | |
| 6,517,478 | B2  | 2/2003 | Khadem | |
| 6,591,130 | B2  | 7/2003 | Shahidi | |
| 7,167,645 | B2 * | 1/2007 | Matsuda et al. | 396/213 |
| 7,170,677 | B1 * | 1/2007 | Bendall et al. | 359/464 |
| 7,179,221 | B2 * | 2/2007 | Tsujita et al. | 600/109 |
| 7,270,422 | B2 * | 9/2007 | Matsuda et al. | 353/70 |
| 7,517,089 | B2 * | 4/2009 | Matsuda | 353/69 |
| 2001/0051761 | A1 * | 12/2001 | Khadem | 600/117 |
| 2003/0035100 | A1 * | 2/2003 | Dimsdale et al. | 356/124 |
| 2004/0021799 | A1 * | 2/2004 | Matsuda | 348/744 |
| 2004/0036813 | A1 * | 2/2004 | Matsuda | 348/744 |
| 2005/0013504 | A1 * | 1/2005 | Noma et al. | 382/255 |
| 2005/0213846 | A1 * | 9/2005 | Matsuda et al. | 382/275 |
| 2006/0176209 | A1 * | 8/2006 | Shu et al. | 342/25 R |
| 2007/0203394 | A1 * | 8/2007 | Wiklof | 600/109 |

* cited by examiner

*Primary Examiner* — John P Leubecker
(74) *Attorney, Agent, or Firm* — McAndrews, Held & Malloy, Ltd.; William Baxter

(57) ABSTRACT

A method and apparatus for calibrating an endoscope includes an endoscope system configured to acquire a first calibration image at a first calibration focal length and determine a radius of a first calibration image boundary corresponding to the first calibration focal length for the first calibration image, wherein the radius of the first calibration image boundary corresponds to a first calibration magnification of the endoscope. A clinical image is acquired at a clinical focal length, wherein the first calibration focal length is different than the clinical focal length and a radius of a clinical image boundary corresponding to the clinical focal length for the clinical image is determined, wherein the radius of the clinical image boundary corresponds to a clinical magnification of the endoscope. The radius of the first calibration image boundary is compared to the radius of the clinical image boundary to determine a change in magnification of the endoscope.

17 Claims, 7 Drawing Sheets

SYSTEMS AND METHODS FOR CALIBRATING AN ENDOSCOPE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to an endoscope. More specifically, the present invention relates to systems and methods for calibrating an endoscope.

Computer-assisted systems and methods now provide real-time navigation during surgical procedures, including analysis and inspection of three-dimensional (3-D) anatomical images from magnetic resonance (MR) and computed tomography (CT) data). Endoscopic technology has also undergone rapid development, providing lightweight endoscopes able to be used in small body cavities. Endoscopes are however able to display only visible surfaces, and are also limited by their inability to provide views of the interior of opaque tissue. The combination of both endoscopic and computer-generated 3-D images has the potential to provide the previously unavailable capability of overlaying volumetrically reconstructed patient images onto the endoscopic view of the surgical field. This technique could permit surgeons to look beyond visible surfaces and provide "on-the-fly" 3-D and two-dimensional (2-D) information for planning and navigational purposes. Due to the many parameters involved in the function of an endoscope, however, multiple small errors in the settings of the device may have relatively large and cumulative effects on the final discrepancy between the position of the overlaid endoscopic images and the patient's anatomy. For this reason, precise calibration of the endoscope and accuracy testing of the calibrated endoscope is necessary to ensure surgical quality.

Thus, there is a need for systems and methods of calibrating an endoscope, an endoscopy system, and/or an augmented endoscopy system.

Image-guided or augmented endoscopy, as described above, is a technique where computer-generated virtual reality representations of endoscopic views can be combined with real-world views to produce "augmented reality." This technique typically requires that the endoscope be tracked in space by well-known methods such as electromagnetic (EM) and/or optical navigation systems. For example, an endoscope calibration fixture may be tracked in space or calibration markers on the fixture may be in a known location with respect to the tracking system.

An advantage of augmented endoscopy is to assist in the visualization of critical structures that may not be evident in real-time endoscopic video images by addressing the relative loss of stereoscopic depth perception and orientation associated with endoscopy. By calibrating the endoscope's position and line of sight to the navigation system and calibrating the endoscope's optical lens parameters (camera calibration), the co-registration of the computer-rendered 3-D virtual representation of the endoscope's field of view could be performed with the endoscopic video image. Depth perception may be augmented, and therefore, healthy and diseased tissue not directly visible to the endoscope may be displayed.

However, the endoscope's optical lens parameters, such as focal length, principal point, radial and tangential distortion, pixel scaling, and field of view, may vary with the magnification of the endoscope. Typically, the magnification of the endoscope is adjusted by rotating a zoom control on the endoscope camera. Unlike surgical microscopes, which typically include optical encoders to determine the amount of zoom or magnification, systems and methods for detecting endoscope magnification do not exist.

Thus, there is also a need for systems and methods for detecting endoscope magnification and calibrating the endoscope, the endoscopy system, and/or the augmented endoscopy system accordingly.

BRIEF SUMMARY OF THE INVENTION

Certain embodiments of the present invention provide a method for calibrating an endoscope. The method includes acquiring a calibration image set, determining a calibration image boundary set for the calibration image set, acquiring a clinical image, and determining a clinical image boundary for the clinical image. A clinical image may be the use of an endoscope to acquire anatomical video images for the purpose of diagnosis or surgery, for example. The calibration image set includes at least one calibration image. The calibration image boundary set includes a calibration image boundary for each calibration image in the calibration image set.

Certain embodiments of the present invention provide a system for calibrating an endoscope. The system includes an endoscope and a processor. The endoscope is adapted to acquire a calibration image set. The calibration image set includes at least one calibration image. The endoscope is also adapted to acquire a clinical image. The processor is adapted to determine a calibration image boundary set for the calibration image set. The calibration image boundary set includes a calibration image boundary for each calibration image in the calibration image set. The processor is also adapted to determine a clinical image boundary for the clinical image.

Certain embodiments of the present invention provide a computer readable medium. The computer readable medium includes a set of instructions for execution on a computer. The set of instructions includes a calibration routine and a clinical routine. The calibration routine is configured to acquire a calibration image set. The calibration image set includes at least one calibration image. The calibration routine is also configured to determine a calibration image boundary set for the calibration image set. The calibration image boundary set includes a calibration image boundary for each calibration image in the calibration image set. The clinical routine is configured to acquire a clinical image. The clinical routine is also configured to determine a clinical image boundary for the clinical image.

Figure 1:
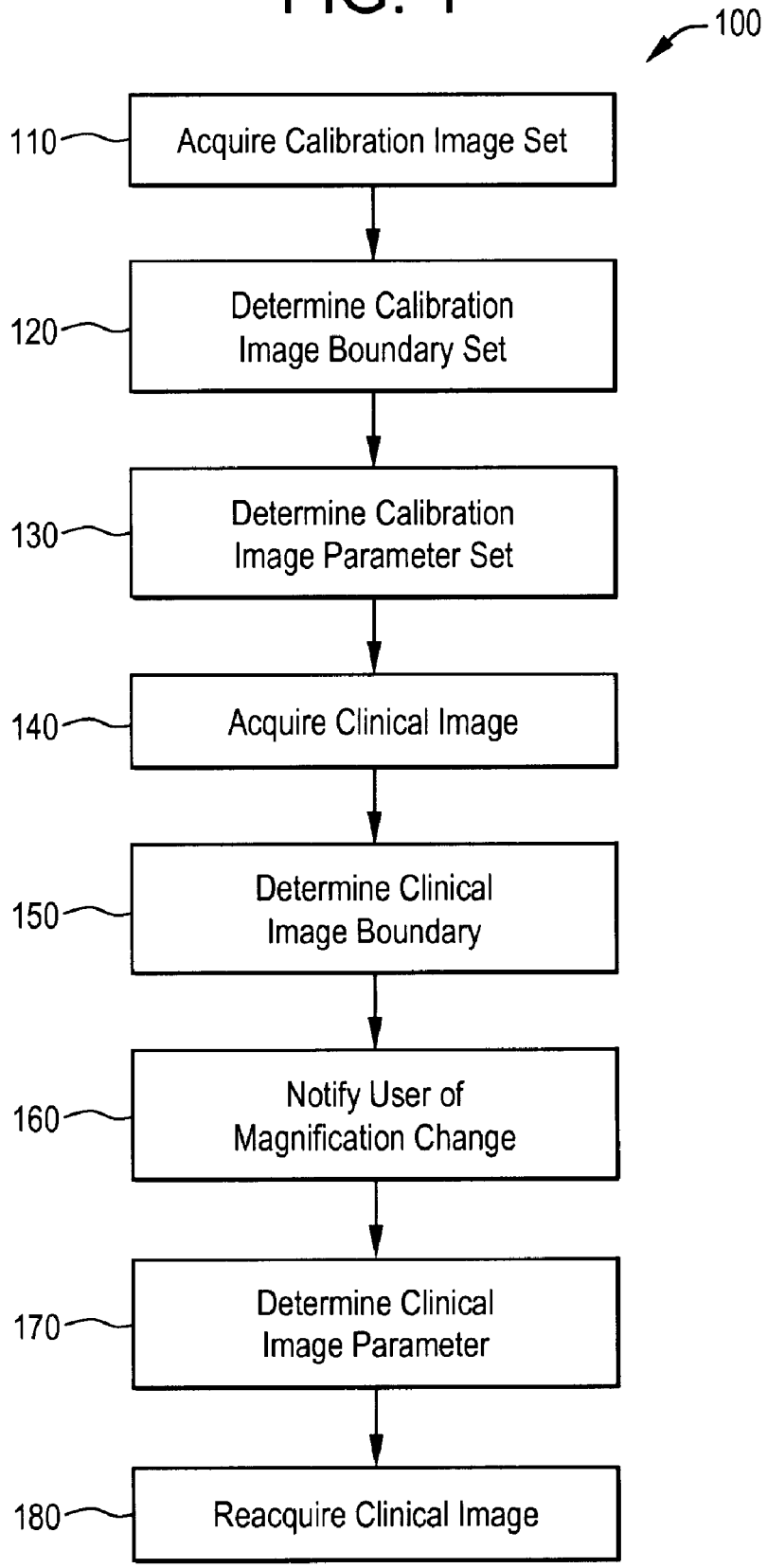
FIG. 1 illustrates a flowchart of a method for calibrating an endoscope according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a flowchart of a method 100 for calibrating an endoscope according to an embodiment of the present invention. The method 100 includes the following steps, which are described in more detail below. At step 110, a calibration image set is acquired. At step 120, a calibration image boundary set is determined. At step 130, a calibration image parameter set may be determined. At step 140, a clinical image is acquired. At step 150, a clinical image boundary is determined. At step 160, a user may be automatically notified of a change in magnification based at least in part on a comparison of the clinical image boundary and the calibration image boundary set. At step 170, a clinical image parameter may be determined based at least in part on the clinical image boundary, the calibration image boundary set, and the calibration image parameter set. At step 180, the clinical image may be reacquired based at least in part on the clinical image parameter.

At step 110, a calibration image set is acquired. The calibration image set may include at least one calibration image. In certain embodiments of the present invention, the calibration image set may include one calibration image. In certain embodiments of the present invention, the calibration image set may include a plurality of calibration images. The calibration image may be, for example, an endoscopic video image acquired using an endoscope, an endoscopy system, and/or an augmented endoscopy system.

Figure 2:
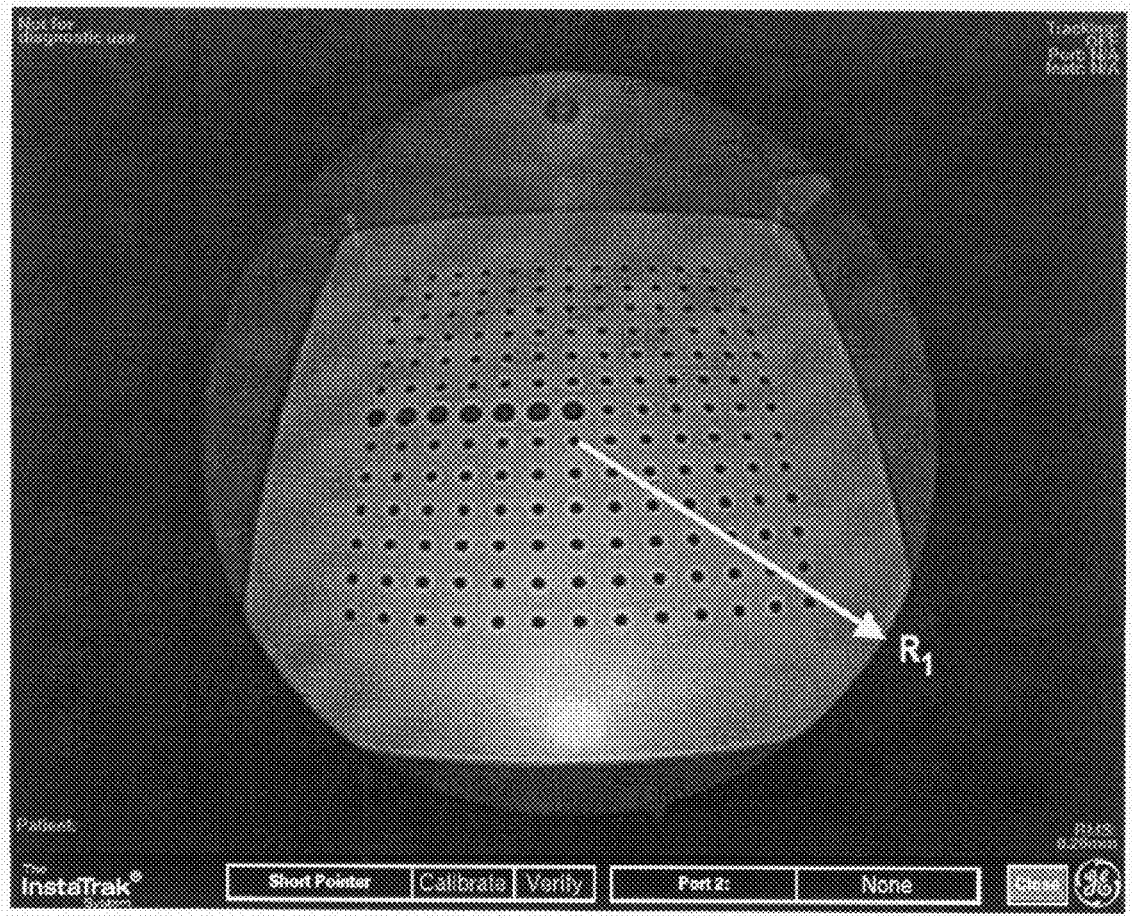
FIG. 2 illustrates an example of an endoscopic video image at a relatively low magnification according to an embodiment of the present invention.
Figure 3:
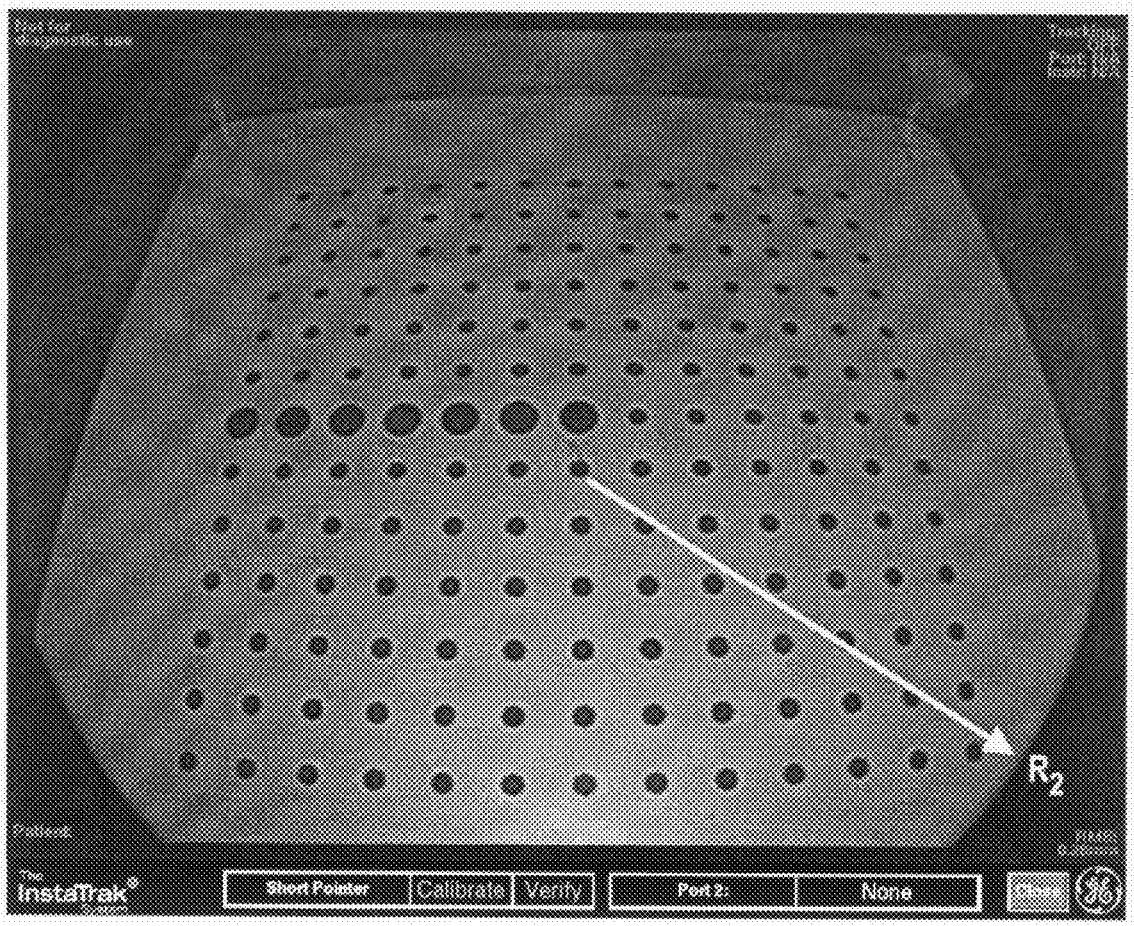
FIG. 3 illustrates an example of an endoscopic video image at a relatively high magnification according to an embodiment of the present invention.

Endoscopic video images are typically displayed as circular images surrounded by black space because the endoscope image, which is circular, is projected onto a rectangular charge-coupled device (CCD). As the endoscopic video image is magnified, the circular image takes up more of the rectangular CCD, and consequently, less of the surrounding black space is displayed. FIG. 2 illustrates an example of an endoscopic video image at a relatively low endoscope magnification according to an embodiment of the present invention. FIG. 3 illustrates an example of an endoscopic video image at a relatively high endoscope magnification according to an embodiment of the present invention.

At step 120, a calibration image boundary set may be determined. The calibration image boundary set may include a calibration image boundary for each calibration image in the calibration image set. In certain embodiments of the present invention, the calibration image boundary may be determined, for example, using image processing techniques. For example, a calibration image, such as the endoscopic video image of FIG. 2, may be thresholded and filtered to find an edge of the calibration image. The edge of the calibration image may be fit to a calibration image boundary, such as a circle and/or another appropriate shape. A circular calibration image boundary may be represented, for example, by a radius R1, as shown in FIG. 2. Calibration image boundaries of other shapes may be represented by other appropriate metrics.

At step 130, a calibration image parameter set may be determined. The calibration image parameter set may include a calibration image parameter for each calibration image in the calibration image set. The calibration image parameter may include, for example, imaging parameters, such as focal length, principal point, radial and tangential lens distortion parameters, pixel scaling, field of view, and/or other imaging parameters.

At step 140, a clinical image is acquired. The clinical image may be, for example, an endoscopic video image acquired using an endoscope, an endoscopy system, and/or an augmented endoscopy system.

At step 150, a clinical image boundary may be determined. In certain embodiments of the present invention, the clinical image boundary may be determined, for example, using image processing techniques. For example, a clinical image, such as the endoscopic video image of FIG. 3, may be thresholded and filtered to find an edge of the clinical image. The edge of the clinical image may be fit to a clinical image boundary, such as a circle and/or another appropriate shape. A circular clinical image boundary may be represented, for example, by a radius R2, as shown in FIG. 3. Clinical image boundaries of other shapes may be represented by other appropriate metrics.

At step 160, a user may be automatically notified of a change in endoscope magnification based at least in part on a comparison of the clinical image boundary and the calibration image boundary set. For example, as shown in FIGS. 2 and 3, the radius R1 of the calibration image boundary may be compared to the radius R2 of the clinical image boundary. If R1≠R2, then the magnification of the endoscope has changed. Further, if R1<R2, then the magnification of the clinical image has increased with respect to the calibration image. Conversely, if R1>R2, then the magnification of the clinical image has decreased with respect to the calibration image.

In certain embodiments of the present invention, if the magnification of the calibration image is known, then the endoscope magnification and/or the change in endoscope magnification may be determined. For example, if R1=200 pixels, R2=400 pixels, and the magnification of the calibration image is 2×, then the magnification of the clinical image is 4×. The endoscope magnification and/or change in endoscope magnification may also be displayed.

In certain embodiments of the present invention, a user may be automatically notified if, for example, the circular image exceeds the rectangular CCD, as described above. However, most users typically prefer a relatively low magnification so that the field of view is as large as possible.

At step 170, a clinical image parameter may be determined based at least in part on the clinical image boundary, the calibration image boundary set, and the calibration image parameter set. Similar to the calibration image parameter, as described above at step 130, the clinical image parameter may include, for example, imaging parameters, such as focal length, principal point, radial and tangential lens distortion parameters, pixel scaling, field of view, and/or other imaging parameters.

In certain embodiments of the present invention, the calibration image boundary set and the calibration image parameter set may be represented as a calibration image parameter table. An example of a calibration image parameter table is provided below in Table 1.

Each row in the calibration image parameter table represents a calibration image in the calibration image set. For example, Table 1 includes three calibration images, each calibration image acquired at a different magnification factor.

Each column in the table represents a calibration image boundary or a calibration image parameter for each calibration image in the calibration image set. For example, Table 1 includes a radius (pixels) for each calibration image in the calibration image set. Table 1 also includes, for example, a focal length (f), a radial distortion (k1), a z-translation (Tz), and a field of view (FOV), for each calibration image in the calibration image set.

TABLE 1

Example of a Calibration Image Parameter Table

| radius (pixels) | f (mm) | k1 (1/mm^2) | Tz (mm) | Tz/f | FOV (degrees) |
|---|---|---|---|---|---|
| 422 | 9.537 | 6.53E−03 | 583.8 | 61.2 | 91.0 |
| 500 | 9.471 | 6.35E−03 | 583 | 61.6 | 101.1 |
| 576 | 9.383 | 5.93E−03 | 591.4 | 63.0 | 109.4 |

In operation, the calibration image parameter table may be used to determine a clinical image parameter. For example, applying the calibration image parameter table in Table 1 to a radius of 420 pixels may result in an estimated focal length of 9.537 millimeters. In this example, the focal length was estimated based on the closest data point (422 pixels) in the calibration image parameter table. As another example, applying the calibration image parameter table in Table 1 to a radius of 461 pixels may result in an estimated focal length of 9.504 millimeters. In this example, the estimated focal length was interpolated based on the two closest data points (422 pixels and 500 pixels) in the calibration image parameter table.

In certain embodiments of the present invention, the calibration image boundary set and the calibration image parameter set may be represented as a calibration image parameter function. An example of a calibration image parameter function is provided in FIG. 7.

In operation, the calibration image parameter function may be used to determine a clinical image parameter. For example, applying the calibration image function in FIG. 7 to a radius of 470 pixels may result in an estimated focal length of 9.495 millimeters. As another example, applying the calibration image parameter function of FIG. 7 to a radius of 560 pixels may result in an estimated focal length of 9.400 millimeters.

Figure 7:
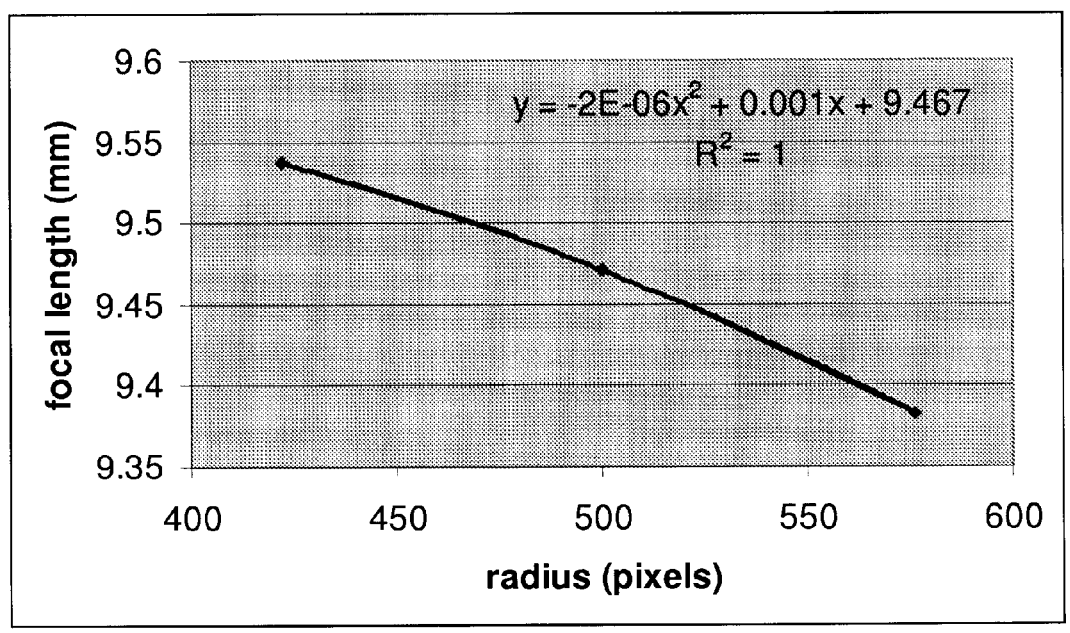
FIG. 7 illustrates an example of a calibration image parameter function according to an embodiment of the present invention.

Although a second-order polynomial was fit to the calibration image parameter table in Table 1 to determine the calibration image parameter function in FIG. 7, other appropriate functions may be fit to the calibration image boundary set and the calibration image parameter set to determine a calibration image parameter function.

In certain embodiments of the present invention, the clinical image parameter may be determined manually, for example, by a user, such as a surgeon, a nurse, a technician, and/or another user. In certain embodiments of the present invention, the clinical image parameter may be determined automatically, for example, by an endoscope, an endoscopic system, and/or another imaging system.

At step 180, the clinical image may be reacquired based at least in part on the clinical image parameter. For example, at an endoscope magnification of 470 pixels, the clinical image may be automatically reacquired at a focal length of 9.495 millimeters.

In certain embodiments of the present invention, the clinical image may be reacquired manually, for example, by a user, such as a surgeon, a nurse, a technician, and/or another user. In certain embodiments of the present invention, the clinical image may be reacquired automatically, for example, by an endoscope, an endoscopic system, and/or another imaging system.

One or more of the steps 110-180 of the method 100 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 4:
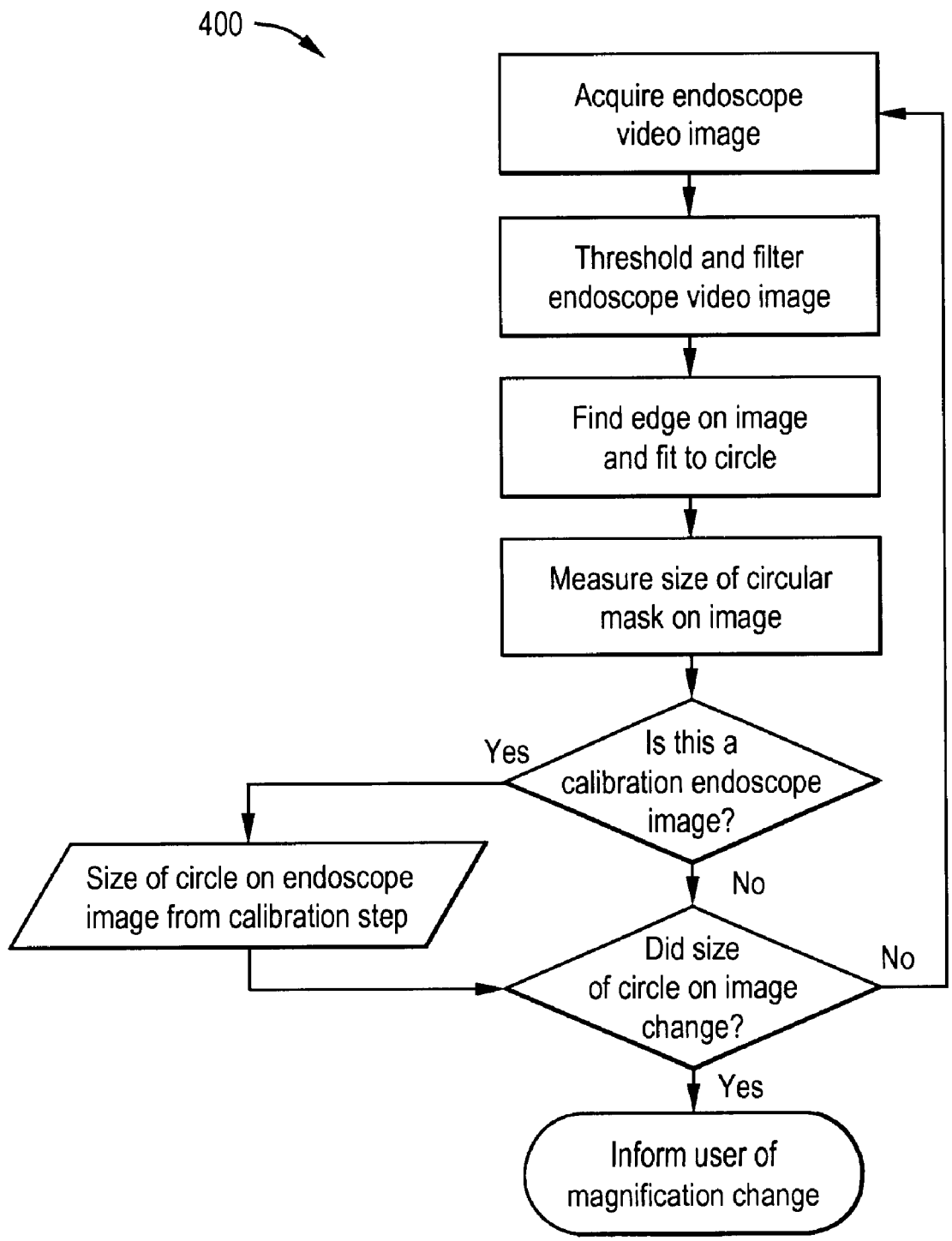
FIG. 4 illustrates a flowchart of a method for detecting endoscope magnification according to an embodiment of the present invention.

FIG. 4 illustrates a flowchart of a method 400 for detecting endoscope magnification according to an embodiment of the present invention. The steps of the method 400 are similar to the steps of the method 100 of FIG. 1, which are described above in more detail.

Figure 5:
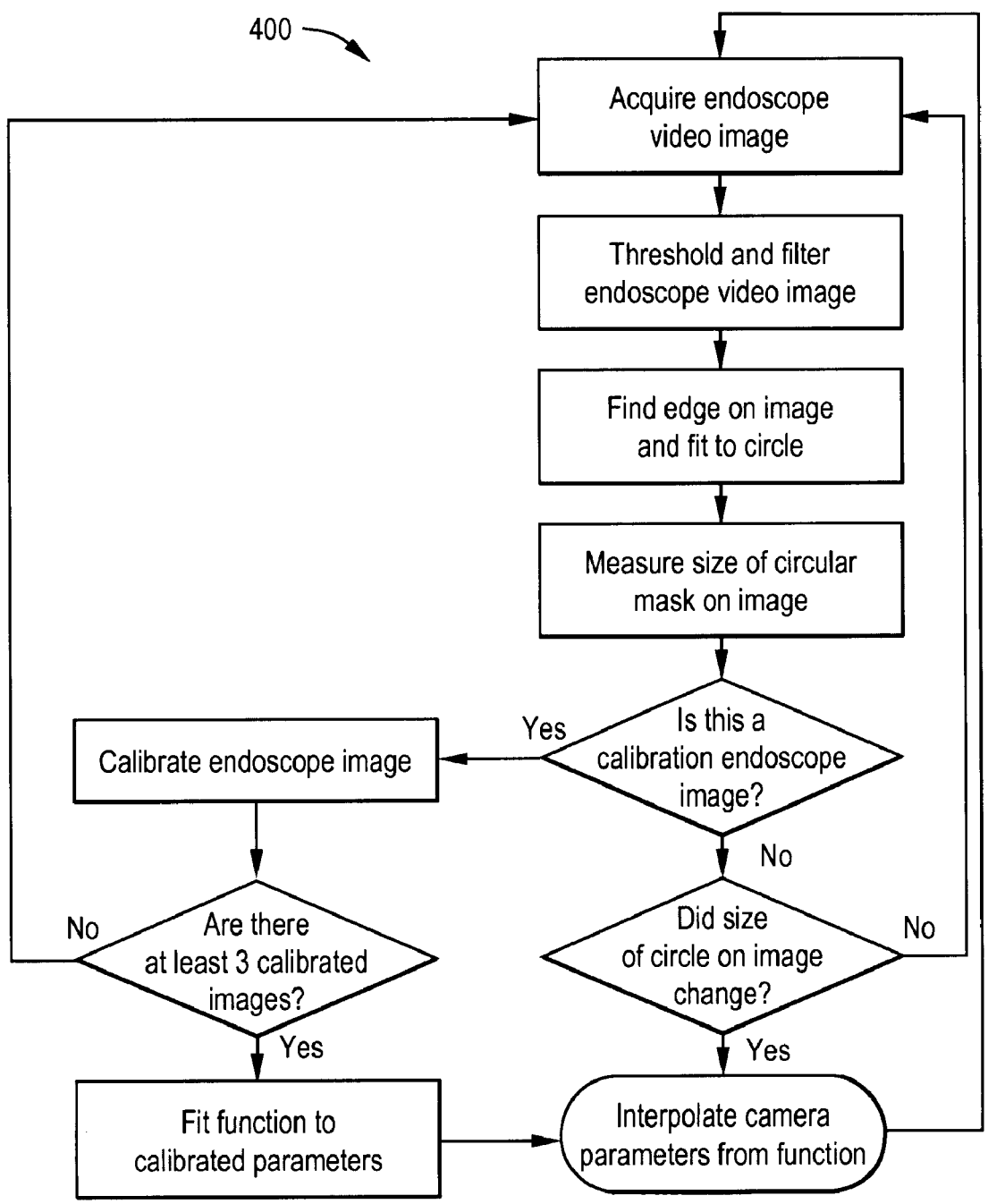
FIG. 5 illustrates a flowchart of a method for calibrating an endoscope according to an embodiment of the present invention.

FIG. 5 illustrates a flowchart of a method 500 for calibrating an endoscope according to an embodiment of the present invention. The steps of the method 500 are similar to the steps of the method 100 of FIG. 1, which are described above in more detail.

Figure 6:
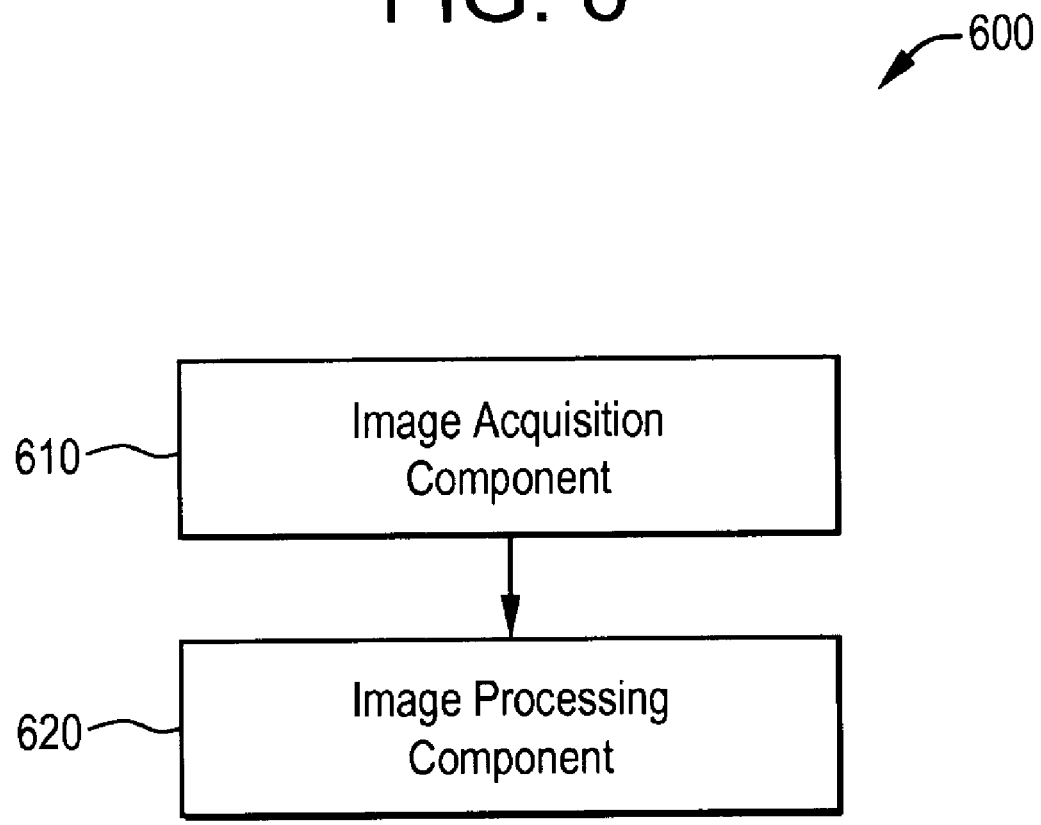
FIG. 6 illustrates a system for calibrating an endoscope according to an embodiment of the present invention.

FIG. 6 illustrates a system 600 for calibrating an endoscope according to an embodiment of the present invention. The system 600 includes an image acquisition component 610 and an image processing component 620. The system 600 is described with reference to the steps 110-180 of the method 100 of FIG. 1, but it should be understood that other implementations are possible.

The image acquisition component 610, such as an endoscope, is adapted to acquire a calibration image set, acquire a clinical image, and/or reacquire the clinical image, as described above at steps 110, 140, and 180 of the method 100 of FIG. 1.

The image processing component 620, such as a central processing unit (CPU) in an endoscopy system or an augmented endoscopy system, is adapted to determine a calibration image boundary set, determine a calibration image parameter set, determine a clinical image boundary, automatically notify a user of a change in endoscope magnification, and/or determine a clinical image parameter, as described above at steps 120, 130, 150, 160, and 170 of the method 100 of FIG. 1.

As discussed above, the components, elements, and/or functionality of the system 600 may be implemented alone or in combination in various forms in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention provide systems and methods for detecting a change in endoscope magnification to alert a user that the calibration of the endoscope is no longer valid.

Certain embodiments of the present invention provide systems and methods for detecting a change in endoscope magnification to adjust the endoscope's optical lens parameters and/or other relevant parameters.

Certain embodiments of the present invention provide systems and methods for calibration of an augmented endoscopy system. For example, a tracking system, such as an electromagnetic (EM) tracking system or an optical tracking system, may track an image acquisition component of an augmented endoscopy system, such as an endoscope. As another example, the tracking system may track a calibrator and/or a location of a calibration image. However, certain embodiments of the present invention are described with respect to augmented endoscopy systems and/or tracking systems, but it should be understood that other implementations are possible. That is, although augmented endoscopy typically requires tracking, certain embodiments of the present invention are not so limited.

As used herein, "endoscope" may refer to an endoscope, an endoscopy system, an augmented endoscopy system, and/or an image acquisition component of an endoscopy system and/or an augmented endoscopy system.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multiprocessor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any medical navigation system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A method for calibrating an endoscope, the method including:
   acquiring a first calibration image at a first calibration focal length;
   determining a radius of a first calibration image boundary corresponding to the first calibration focal length for the first calibration image, wherein the radius of the first calibration image boundary corresponds to a first calibration magnification of the endoscope;
acquiring a clinical image at a clinical focal length, wherein the first calibration focal length is different than the clinical focal length;
determining a radius of a clinical image boundary corresponding to the clinical focal length for the clinical image, wherein the radius of the clinical image boundary corresponds to a clinical magnification of the endoscope; and
comparing the radius of the first calibration image boundary to the radius of the clinical image boundary to determine a change in magnification of the endoscope.

2. The method of claim 1, further including estimating a clinical imaging parameter according to the change in magnification of the endoscope.

3. The method of claim 2,
wherein a first value of a calibration imaging parameter corresponds to the radius of the first calibration image boundary, and
wherein the step of determining a clinical imaging parameter further comprises calculating the clinical imaging parameter according to the first value of the calibration imaging parameter and the change in magnification of the endoscope.

4. The method of claim 3, wherein the calibration imaging parameter comprises at least one of a focal length, a radial distortion, a z-translation, or a field of view.

5. The method of claim 1, further comprising:
acquiring a second calibration image at a second calibration focal length;
determining a second calibration image boundary for the second calibration image, wherein a radius of the second calibration image boundary corresponds to a second calibration magnification of the endoscope.

6. The method of claim 5, further comprising determining a clinical imaging parameter according to the radius of the first calibration image boundary, the radius of the second calibration image boundary, and the change in magnification of the endoscope.

7. The method of claim 6, wherein:
wherein a first value of a calibration imaging parameter corresponds to the radius of the first calibration image boundary;
wherein a second value of the calibration imaging parameter corresponds to the radius of the second calibration image boundary; and
wherein the step of determining a clinical imaging parameter further comprises calculating the clinical imaging parameter according to the first value of the calibration imaging parameter, the second value of the calibration imaging parameter, and the change in magnification of the endoscope.

8. The method of claim 7,
wherein a calibration image parameter function is defined at least by the first value of the calibration imaging parameter, the second value of the calibration imaging parameter, the radius of the first calibration image boundary, the radius of the second image boundary, and the radius of the clinical image boundary, and
wherein the step of determining a clinical imaging parameter further comprises applying the calibration image parameter function.

9. The method of claim 1, wherein the step of determining a first clinical mage boundary further comprises thresholding and filtering the clinical image.

10. A system for calibrating an endoscope, the system including:
an endoscope configured to acquire a clinical image at a clinical focal length and a first calibration image at a first calibration focal length, wherein the first calibration focal length is different than the clinical focal length; and
a processor configured to:
determine a radius of a first calibration image boundary corresponding to the first calibration focal length for the first calibration image, determine a radius of a clinical image boundary corresponding to the clinical focal length for the clinical image, and
determine a change in a magnification of the endoscope according to the radius of the first calibration image boundary and the radius of the clinical image boundary.

11. The system of claim 10, wherein the processor is further configured to determine a clinical imaging parameter according to the change in magnification of the endoscope.

12. The system of claim 10,
wherein a first value of a calibration imaging parameter corresponds to the radius of the first calibration image boundary, and
wherein the step of determining a clinical imaging parameter further comprises calculating the clinical imaging parameter according to the first value of the calibration imaging parameter and the change in magnification of the endoscope.

13. The system of claim 10, wherein the calibration imaging parameter comprises at least one of a focal length, a radial distortion, a z-translation, or a field of view.

14. A computer readable medium including a set of instructions for execution on a computer, the set of instructions including:
a calibration routine configured to:
acquire from an endoscope a first calibration image at a first calibration focal length, and
determine radius of a first calibration image boundary corresponding to the first calibration focal length for the first calibration image; and
a clinical routine configured to:
acquire from the endoscope a clinical image at a clinical focal length, wherein the clinical focal length is different than the first calibration focal length,
determine a radius of a clinical image boundary corresponding to the clinical focal length for the clinical image,
compare a radius of the first calibration image boundary to a radius of the clinical image boundary, and
determine a change in magnification of the endoscope.

15. The set of instructions of claim 14, wherein the clinical routine is further configured to determine a clinical imaging parameter according to the change in magnification of the endoscope.

16. The set of instructions of claim 14,
wherein a first value of a calibration imaging parameter corresponds to the radius of the first calibration image boundary, and
wherein the clinical routine is further configured to calculate the clinical imaging parameter according to the first value of the calibration imaging parameter and the change in magnification of the endoscope.

17. The set of instructions of claim 14, wherein the calibration imaging parameter comprises at least one of a focal length, a radial distortion, a z-translation, or a field of view.

* * * * *